United States Patent [19]

Everhardus et al.

[11] Patent Number: 4,543,310
[45] Date of Patent: Sep. 24, 1985

[54] ELECTROPHOTOGRAPHIC ELEMENT AND PHOTOCOPYING PROCESS MAKING USE OF CERTAIN 4-[BIS-PHENYLAMINO]BENZALDEHYDE AZINES

[75] Inventors: Roelof H. Everhardus, Lomm; Gerard J. E. H. van Lomm, Tegelen, both of Netherlands

[73] Assignee: Océ-Nederland B.V., Venlo, Netherlands

[21] Appl. No.: 459,382

[22] Filed: Jan. 20, 1983

[30] Foreign Application Priority Data

Jan. 29, 1982 [NL] Netherlands ............... 8200331

[51] Int. Cl.$^4$ ............... G03G 5/06; G03G 5/14; C09C 109/12
[52] U.S. Cl. ............... 430/59; 430/126; 430/134; 430/74
[58] Field of Search ............... 430/58, 59, 74, 126, 430/134

[56] References Cited

U.S. PATENT DOCUMENTS

| | | | |
|---|---|---|---|
| 3,290,147 | 12/1966 | Mattor et al. | 96/1 |
| 3,613,820 | 1/1973 | Champ et al. | 96/1.5 |
| 3,725,058 | 4/1973 | Hayashi et al. | 96/1.5 |
| 3,824,099 | 7/1974 | Champ et al. | 96/1.5 |
| 3,837,851 | 9/1974 | Shattuck et al. | 96/1.5 |
| 3,839,034 | 10/1974 | Widemann | 96/1.5 |
| 3,898,084 | 8/1975 | Champ et al. | 96/1.5 |
| 4,378,415 | 3/1983 | Chu et al. | 430/58 |
| 4,399,207 | 8/1983 | Sakai et al. | 430/58 |

FOREIGN PATENT DOCUMENTS

| | | |
|---|---|---|
| 2438858 | 5/1979 | France . |
| 54-83435 | 3/1979 | Japan . |
| 6409093 | 2/1965 | Netherlands . |

OTHER PUBLICATIONS

Patents Abstracts of Japan, vol. 3, No. 106, p. 96 re Kokai No. 54-83435.

*Primary Examiner*—John L. Goodrow
*Attorney, Agent, or Firm*—Albert C. Johnston

[57] ABSTRACT

A multi-layered electrophotographic element providing significantly improved properties, and especially so for use as a "permanent" master in transfer photocopying, comprises a conductive support carrying a photoconductive charge generating layer and on top of the photoconductive layer a charge transporting layer containing homogeneously distributed in an insulating binder a charge transporting agent selected from among certain azines which may comprise one or more alkylsubstituents and/or heterocyclic groups with at least one nitrogen atom and/or phenyl or naphthyl groups. The charge transporting layer may also contain to advantage an activator for the charge transporting agent. Particularly effective activators are terephthalal dimalonitrile (TDM) and 1,3,7- trinitro-dibenzothiophene-5,5-dioxide (DBTO). The charge transporting layer preferably is applied to a very thin charge generating layer formed on an endless support, and which contains the charge generating compound in molecularly divided form. Photocopying can be carried out with enhanced permanence of the usefulness of the element by charging the element for each copying operation to not more than about 70% of its maximum chargeable surface voltage.

20 Claims, No Drawings

ELECTROPHOTOGRAPHIC ELEMENT AND PHOTOCOPYING PROCESS MAKING USE OF CERTAIN 4-[BIS-PHENYLAMINO]BENZALDEHYDE AZINES

This invention relates to a multi-layered electrophotographic element and to a method of photocopying by use of the element.

In electrophotography, an image is formed on an electrophotographic element comprising a photoconductive layer by first providing the surface of that layer with a uniform electrostatic charge and then exposing it imagewise to light The imagewise exposure causes the areas struck by light to become conductive and discharged, and the charge remaining in the non-exposed areas forms an electrostatic latent image. This latent image is rendered visible, for example, by depositing onto the layer surface finely divided electroscopic toner particles which are attracted by the remaining charge.

In direct electrophotography, the image thus rendered visible is fixed locally onto the photoconductive layer, e.g. by heat and/or pressure. In indirect electrophotography, the image formed on the photoconductive element is first transferred to and then is fixed onto a support, usually of plain paper; whereupon any toner particles remaining on the photoconductive layer surface are cleaned from it to make the element suitable for a subsequent copying cycle.

The electrophotographic element in practice may consist of a radiation-sensitive charge generating layer applied to a conductive support. Alternatively it may comprise a plurality of layers including a radiation-sensitive charge generating layer and a charge transporting layer applied thereto. Such multi-layered electrophotographic elements are described, for example, in U.S. Pat. Nos. 3,713,820, 3,725,058, 3,824,099, 3,837,851, 3,839,034 and 3,898,084.

The radiation-sensitive compound or compounds in the charge generating layer may be of inorganic or organic nature. When inorganic material is used, it generally is present either in the form of particles dispersed in a binder or in the form of a homogeneous film obtained, for example, by vapor deposition. Selenium is the inorganic material most commonly used. When organic material is used, it may, for example, be present in the form of a film-forming organic polymer, such for example as polyvinyl carbazole or polyvinyl pyrene, or in the form of finely divided pigment particles, such for example as bisazo pigments of which Phenelac Blue and it derivatives are among the best known, which are dispersed in an organic binder.

Such pigment-binder layers, however, have exhibited a number of disadvantages; hence, processes have been proposed for preparing charge generating layers in which the radiation-sensitive compound is present in molecularly divided form instead of in the form of pigment particles. The advantage of the former is that the layers can be much thinner and smoother than pigment-binder layers and can also be better in respect of their charge transport and resolving powers. Furthermore, the grinding operations required for the preparation of pigment-binder layer compositions can be dispensed with.

Charge generating layers containing radiation-sensitive compounds in molecularly divided form are described, for example, in U.S. Pat. Nos. 4,123,270 and 4,286,040 and in U.K. Pat. No. 1 172 355.

When, because of the associated advantages, it is desired to use such layers in the thinnest possible form, e.g. in a thickness of not more than 1 to 2 $\mu$m, they must be provided with a top layer because of the vulnerability of the extremely thin layers to abrasion, and in order to be able to bring them to the required charge level during uniform charging. The top layer to be used must also permit the transport of one of the two charge carriers, usually holes, which are formed in the charge generating layer during the imagewise exposure. Thus, the top layer is required to satisfy very high requirements.

Numerous kinds of charge transporting layers have been proposed in the prior art. Generally they can be considered as being of two main types. The charge transporting layers of one type are formed by polymeric film-forming compounds which themselves have charge transporting properties, such for example as polyvinyl carbazole or polyvinyl pyrene. Layers of the other types are formed by charge transporting compounds dissolved in a binder which of itself is insulating. Examples of these can be found in the above-mentioned U.S. and U.K. patents. Charge transporting layers of this type in many cases also contain a so-called activator which improves the charge transporting properties of the layer. Among the known activators are, for example, the electron acceptors trinitrofluorenone and dibenzothiophene dioxide.

A charge transporting layer should exhibit each and all of the following properties:
mechanically strong,
smooth surface and good filmforming properties,
transparent to visible light,
good adhesion to the generation layer,
good retention of the electrostatic surface charge in the dark,
adapted to be charged to a sufficient level,
capable of transporting holes (or electrons) satisfactorily,
have no or practically no injection barrier with the generation layer,
good cleaning properties, and
low residual charge after exposure.

The charge transporting layers hiterto proposed fall short with respect to one or more of the above properties, so that they are less than satisfactory, particularly when applied on very thin charge generating layers.

The object of the present invention is to provide a multi-layered electrophotographic element with a charge transporting layer which to a very high degree satisfies all the above noted properties and in respect of its low residual charge, cleaning properties, and practical absence of an injection barrier, is far superior to any of the hitherto known charge transporting layers, so that it is particularly advantageous in use on a very thin charge generating layer.

The multi-layered electrophotographic element according to the invention comprises an electrically conductive support carrying a photoconductive layer that comprises one or more radiation-sensitive charge generating compounds, and carrying on the photoconductive layer a charge transporting layer formed of an insulating binder having homogeneously distributed therein as a charge transporting agent a compound, or a mixture of compounds, having the general formula 1 shown on the Formula sheet infra, wherein $R_1$ and $R_2$, which may be the same or different, each represents a hydrogen atom, or an alkyl, aryl or aralkyl group, whilst $A_1$ and $A_2$, which may be the same or different, each represents a heterocyclic group which comprises at least one nitrogen atom, such as e.g. N-alkylcarbazole-3-yl, 4,5-diphenyloxazole-2-yl or benzothiazole-2-yl, or a phenyl or naphthyl group, which may be substituted with a lower alkyl, a lower alkoxy group or halogen and at least one of which also comprises, and in case of a phenyl group preferably in the para-position, the electron donating group

in which $R_3$ and $R_4$, which may be the same or different, represent alkyl or phenyl groups, which may be substituted, or, together with the nitrogen atom are forming a heterocyclic ring or are part of a condensed heterocyclic ring system.

The symmetrical and asymmetrical azines according to structural formula 1 can be synthesized by generally known methods for related compounds, such as e.g. described in Houben—Weyl, Methoden der organischen Chemie, 4th edition, Vol. 10/2, pages 89 to 111, published by Georg Thieme Verlag, Stuttgart in 1967.

Examples of charge transporting compounds which belong to the above defined classes are shown in the structural formulas 2–11 of the formula sheet.

Very good results were obtained with compounds of general structural formula 1 in which $R_1$ and $R_2$ are hydrogen and $A_1$ and $A_2$ are a phenyl group and which comply with the general structural formula 12 of the formula sheet, wherein $R_5$ to $R_{10}$ each represents a hydrogen atom or an alkyl group having 1 to 4 carbon atoms.

An example of a compound which has proved to be well usable is the one having the structural formula 12 in which $R_5$ to $R_{10}$ are hydrogen atoms, and compounds according to the structural formula 1 in which $R_5$, $R_6$, $R_8$ and $R_9$ are hydrogen atoms and $R_7$ and $R_{10}$ are alkyl groups.

Preference, however, is given to compounds of the general structural formula 12 in which $R_5$, $R_6$, $R_8$ and $R_9$ represent alkyl groups in the para or meta position. Particularly good results were obtained with the compound belonging to this group according to structural formula 13 of the formula sheet.

Electrophotographic elements in which the charge transporting layer comprises that compound, viz, 4-[bis(4-methyl-phenyl)amino] benzaldehyde, azine as the charge transporting agent show a high photosensitivity, a very low residual charge after exposure and a low dark decay even when they are charged to not more than 30–70% of their maximum apparent surface voltage ($ASV_{max}$). This aspect of the invention is of great advantage since electrophotographic elements which are charged to a level well below their $ASV_{max}$ have a substantially greater permanence of usefulnes than elements which are charged to their $ASV_{max}$. Furthermore, in uses of the elements according to the invention cleaning of the charge transporting layer after transfer of the developed image was found to involve no problems, contrary to the case of multi-layered elements of the type concerned in which the charge transporting layer contained one of the hitherto known charge transporting agents.

The quantity of charge transporting agent to be used in the charge transporting layer of the electrophotographic elements according to the invention may vary within wide limits, but it generally lies between 15% and 70% by weight, based on the total quantity of solids, and preferably is between 20% and 40% by weight.

The insulating binder to be used for the charge transporting layer may be any polymeric material suitable for that purpose. Examples of suitable binder materials are polystyrenes, silicone resins, polyesters of acrylic and methacrylic acid, vinyl polymers and vinyl copolymers. Particularly good results are obtained with polycarbonate resins because of their high transparency, mechanical strength and good adhesion to the photosensitive layer.

The support to be used can be selected from among the various supports known for use in electrophotographic elements. Such supports may be conductive of themselves, e.g. supports of aluminium, steel or nickel, or they may be rendered conductive, such as in the case of paper or plastic supports to which a thin conductive layer, e.g. of aluminium or nickel, has been applied. The present invention is eminently suited for use in indirect electrophotography in the form of an endless element the support of which is, for example, a drum or a flexible web of paper or plastic having its ends joined together.

The radiation-sensitive charge generating compound to be used in the photoconductive layer of the electrophotographic element may be either inorganic or organic in nature. Examples of inorganic compounds are selenium and amorphous silicon.

Preferably, however, organic compounds and more particularly radiation-sensitive bisazo compounds are employed. Examples of radiation-sensitive layers containing one or more bisazo compounds in molecularly divided form are found in the above-mentioned U.S. Pat. No. 4,123,270 and in U.S. Pat. No. 4,286,040.

The thickness of the photoconductive layer is preferably between about 0.2 and 2 μm.

It usually is advantageous in carrying out the invention to incorporate one or more activators in the charge transporting layer of the electrophotographic element. This particularly is the case when it is desired to charge the electrophotographic element only partially, say to 30–70% of its $ASV_{max}$, in order to enhance permanence, as an activator will improve the discharge characteristic of the element. In principle, any of the known activators can be used for this purpose. Examples of suitable activators are trinitrofluorenone, the dibenzothiophene oxides mentioned in U.S. Pat. No. 3,905,814 and the N-(fluoren-9-ylidene)anilines mentioned in U.S. Pat. No. 3,935,009.

Particularly good results have been obtained with the activators terephthalal dimalonitrile (TDM; formula 14 of the Formula sheet) and 1,3,7-trinitro-dibenzothiophene-5, 5-dioxide (DBTO; formula 22 of the Formula sheet). Unlike many of the activators used hitherto, TDM is in addition absolutely non-mutagenic.

The quantity of activator to be used is generally between 1 and 15% by weight based on the charge transporting agent.

When TDM is used in combination with a charge transporting agent according to the invention, it has been found that quantities of TDM of between 0.5 and 3% by weight are sufficient for the desired results.

The electrophotographic element according to the invention can be prepared by known methods. The patents referred to hereinbefore describe in detail methods suitable for the preparation of both the charge generating layer and the charge transporting layer.

The azines according to the general structural formula 12 of the Formula sheet, which preferably are used in the charge transporting layer can be synthesized by condensation of the corresponding p-(diarylamino)-benzaldehydes, which may or may not contain alkyl groups, with hydrazine. The preparation method is similar to that of the condensation of p-(dimethylamino)-benzaldehyde and hydrazine as described in Beilstein (Basic Series) 14, 36.

Most of the aldehydes referred to can be prepared by formulation of the corresponding triarylamines by means of N,N-dimethylformamide and phosphoroxytrichloride. The reactions of these can be carried out similarly to the preparation of p-(dimethylamino) benzaldehyde (Org. Synth. Coll. Vol. IV, p. 331). The preparation of p-(diphenylamino) benzaldehyde is described in J. Org. Chem. 30, 3714 (1965).

Electrophotographic elements of the invention that comprise a charge transporting layer applied to a thin charge generating layer are eminently suitable for use as a so-called permanent master in an indirect electrophotographic copying machine. It is precisely here that their particular advantages referred to hereinbefore are fully manifest, and copies of high quality can be obtained even with partial charging.

The latent image formed in the conventional manner on the charge transporting layer can be rendered visible by use of either a two-component or a one-component developer. In the former case the developer consists of coarser carrier particles, usually iron particles, and very finely divided toner particles which acquire the required polarity by contact with the carrier particles. In the second case the developer consists essentially of finely divided toner particles which may be conductive (resistivity $<10^{10}$ Ohm.m) or insulating (resistivity $>10^{10}$ Ohm.m).

The electrophotographic element according to the invention is found to be particularly well suited for development by means of a one-component developer, and this has a number of advantages. When an insulating one-component developer is used, however, it has been found desirable to provide the electrophotographic element with a function layer in the form of a raster. Layers of this kind and the location and method of applying them are known to those skilled in the art and are described, inter alia, in "Xerography and related processes" by Dessauer and Clark, 1965, pp. 11–117.

The practice and advantages of the invention will be further understood from the following illustrative examples.

EXAMPLE 1

Preparation of a charge generating layer. A charge generating layer was prepared which contained as charge generating compound the bisazo dye 4,4'[(3,3'-dimethoxy[1,1'-biphenyl]-4,4'-diyl)bis(azo)]bis[3-hydroxy-N-phenyl-2-naphthalene carboxamide](formula 17 of the Formula sheet) distributed in molecularly divided form in a binder. For that purpose the following solutions were first prepared:

60 ml of 2% polymeric cellulose acetate butyrate in acetone, 13 ml of N,N-dimethylformamide +1 g of the naphthol of formula 15 of the Formula sheet, and 7 ml of N,N-dimethylformamide +0.5 g of a diazonium compound according to formula 16 of the Formula sheet.

The resulting bisazo compound-binder solution, after 10 minutes storage in the dark, was applied to a conductive support (Melinex with a vapor-deposited aluminium coating) by dip-coating at 25° to 30° C. and 30–40% relative humidity. After drying, the in-situ coupling to the above-mentioned bisazo compound was effected in an ammonia development unit.

The thickness of the resultant charge generating layer was 0.5 μm.

EXAMPLE 2

A charge transporting layer comprising as the charge transporting compound the azine of formula 13 of the Formula sheet was applied by dip-coating to a charge generating layer prepared according to Example 1.

Application was effected by use of a solution of 25 ml of 10% "Lexan 141" (a polycarbonate resin from General Electric) in 1,2-dichloroethane, 1.5 g of the said azine and 8 ml of tetrahydrofuran. After 15 minutes drying to the air the resulting double layer was dried in vacuo at 135° C. for 30 minutes.

By use of the resulting multi-layered electrophotographic element photocopies were made in an indirect electrophotographic photocopying machine, and the following points were checked: layer thickness; adhesion of the layers; charging; dark-decay; light-sensitivity; surface charge density; residual potential; memory effect; image quality of the copy obtained after transfer to plain paper, such transfer being of an image rendered visible on the charge transporting layer by application of a one-component developer, followed by fixation by heat and pressure; cleanability of the charge transporting layer; and permanence.

The results obtained with the electrophotographic element according to this example, and the results obtained with element according to the Examples 3 to 15, are summarized after Example 15.

EXAMPLE 3

Same as Example 2 except that 0.02 g of the activator TDM (formula 14 of the Formula sheet) was dissolved in the 8 ml of tetrahydrofuran.

EXAMPLE 4

Same as Example 2 except that 0.12 g of the activator TDM (formula 14 of the Formula sheet) was dissolved in the 8 ml of tetrahydrofuran.

EXAMPLE 5

Same as Example 2 except that 0.02 g of the activator DBTO (formula 22 of the Formula sheet) was dissolved in the 8 ml of tetrahydrofuran.

EXAMPLE 6

Same as Example 2 except that 0.12 g of the activator DBTO (formula 22 of the Formula sheet) was dissolved in the 8 ml of tetrahydrofuran.

EXAMPLE 7

Same as Example 2 except that the azine of formula 13 of the Formula sheet was replaced by the azine of formula 18 of the Formula sheet and 0.02 g of the activator TDM (formula 14 of the Formula sheet) was dissolved in the 8 ml of tetrahydrofuran.

EXAMPLE 8

Same as Example 2 except that the azine of formula 13 of the Formula sheet was replaced by the azine of formula 19 of the Formula sheet and 0.02 g of the activator TDM (formula 14 of the Formula sheet) was dissolved in the 8 ml of tetrahydrofuran. For better dissolution of the azine 7 ml of 1,2-dichloroethane were also added.

EXAMPLE 9

Same as Example 2 except that the azine referred to therein was replaced by 0.75 g of the azine of formula 20 of the Formula sheet and 0.01 g of the activator TDM (formula 14 of the Formula sheet) was dissolved in the 8 ml of tetrahydrofuran.

EXAMPLE 10

(Comparative Example)

Same as Example 2 except that the azine of formula 13 of the Formula sheet was replaced by the oxadiazole of formula 21 of the Formula sheet and no tetrahydrofuran was added.

EXAMPLE 11

(Comparative Example)

Same as Example 2 except that the azine of formula 13 of the Formula sheet was replaced by the oxadiazole of formula 21 of the Formula sheet and 0.02 g of the activator TDM (formula 14 of the Formula sheet) was dissolved in the 8 ml of tetrahydrofuran.

EXAMPLE 12

(Comparative Example)

Same as Example 2 except that the azine of formula 13 of the Formula sheet was replaced by the oxadiazole of formula 21 of the Formula sheet and 0.12 g of TDM (formula 14 of the Formula sheet) was dissolved in the 8 ml of tetrahydrofuran.

EXAMPLE 13

(Comparative Example)

Same as Example 2 except that the azine of formula 13 of the Formula sheet was replaced by the triarylmethane of formula 23 of the Formula sheet.

EXAMPLE 14

(Comparative Example)

Same as example 2 except that the azine of formula 13 of the Formula sheet was replaced by the triarylmethane of formula 23 of the formula sheet and 0.02 g of the activator TDM (formula 14 of the Formula sheet) was dissolved in the 8 ml of tetrahydrofuran.

EXAMPLE 15

(Comparative Example)

Same as Example 2 except that the azine of formula 13 of the Formula sheet was replaced by the triarylmethane of formula 23 of the Formula sheet and 0.12 g of the activator TDM (formula 14 of the Formula sheet) was dissolved in the 8 ml of tetrahydrofuran.

RESULTS OF EXAMPLES 2 to 15

The charge transporting layers of these examples were all 3 to 4 μm thick. The adhesion of the layers was excellent. The memory effect of the fully charged layers of Examples 2 to 15 was very low, and on partial charging memory effect was completely absent. The copy quality for both full and partial charging of the layers of Examples 7 and 9 to 15 was good, and of the layers of Examples 2,3,4, 5,6 and 8 was excellent. For all layers the permanence upon partial charging was considerably higher than upon full charging. The layers of Examples 2 to 9 could all be cleaned easily when a one-component developer was used for the development of the latent electrostatic image, while the layers of the comparative Examples 10 to 15 could be cleaned only with great difficulties.

The photoelectric results upon full charging are summarized in Table 1 below. The photoelectric results upon partial charging are summarized in Table 2 below.

TABLE 1

| | Charge transporting layer | | Maximum charging | | | | residual % |
|---|---|---|---|---|---|---|---|
| Example | Charge transporting agent | Activator | ASV volts | DD-1 % | L-25 mJ/m$^2$ | sigma mC/m$^2$ | |
| 2 | 1.5 g formula 13 | — | −437 | 13 | 44 | 4.1 | 5 |
| 3 | 1.5 g formula 13 | 0.02 g TDM | −501 | 12 | 33 | 4.3 | 5 |
| 4 | 1.5 g formula 13 | 0.12 g TDM | −417 | 13 | 30 | 4.2 | 4 |
| 5 | 1.5 g formula 13 | 0.02 g DBTO | −519 | 10 | 38 | 4.5 | 4 |
| 6 | 1.5 g formula 13 | 0.12 g DBTO | −445 | 12 | 36 | 4.3 | 3 |
| 7 | 1.5 g formula 18 | 0.02 g TDM | −547 | 8 | 54 | 4.7 | 10 |
| 8 | 1.5 g formula 19 | 0.02 g TDM | −341 | 11 | 33 | 4.5 | 7 |
| 9 | 0.75 g formula 20 | 0.01 g TDM | −450 | 9 | 60 | 4.5 | 13 |
| 10 | 1.5 g formula 21 | — | −422 | 12 | 56 | 4.2 | 11 |
| 11 | 1.5 g formula 21 | 0.02 g TDM | −369 | 13 | 36 | 4.1 | 8 |
| 12 | 1.5 g formula 21 | 0.12 g TDM | −344 | 13 | 52 | 4.2 | 7 |
| 13 | 1.5 g formula 23 | — | −420 | 12 | 56 | 4.2 | 7 |
| 14 | 1.5 g formula 23 | 0.02 g TDM | −412 | 13 | 43 | 4.1 | 6 |
| 15 | 1.5 g formula 23 | 0.12 g TDM | −355 | 10 | 47 | 4.1 | 10 |

ASV: Apparent surface voltage in volts after charging.
DD-1: Dark decay in the first second as a percentage of the ASV.
L-25: Quantity of light in mJ/m$^2$ in order to discharge the layer with a BRAUN flash type F900 to 25% of the ASV.
sigma: Surface charge density in mC/m$^2$, measured after 1 second dark decay.
Residual: Percentage of the ASV remaining after exposure with 100 mJ/m$^2$ (BRAUN flash type F900)

TABLE 2

| | Charge transporting layer | | Partial charging (about 280 Volts) | | | | |
|---|---|---|---|---|---|---|---|
| Example | Charge transporting agent | Activator | ASV volts | DD-1 % | L-25 mJ/m$^2$ | sigma mC/m$^2$ | residual % |
| 2 | 1.5 g formula 13 | — | −285 | 3 | 44 | 2.5 | 6 |
| 3 | 1.5 g formula 13 | 0.02 g TDM | −273 | 2 | 30 | 2.4 | 6 |
| 4 | 1.5 g formula 13 | 0.12 g TDM | −288 | 5 | 26 | 2.9 | 6 |
| 5 | 1.5 g formula 13 | 0.02 g DBTO | −289 | 3 | 32 | 2.5 | 5 |
| 6 | 1.5 g formula 13 | 0.12 g DBTO | −282 | 2 | 33 | 2.6 | 5 |
| 7 | 1.5 g formula 18 | 0.02 g TDM | −287 | 5 | 40 | 2.3 | 16 |
| 8 | 1.5 g formula 19 | 0.02 g TDM | −280 | 7 | 30 | 3.5 | 6 |
| 9 | 0.75 g formula 20 | 0.01 g TDM | −282 | 5 | 50 | 3.1 | 8 |
| 10 | 1.5 g formula 21 | — | −281 | 2 | 70 | 2.7 | 16 |
| 11 | 1.5 g formula 21 | 0.02 g TDM | −285 | 3 | 33 | 3.1 | 9 |
| 12 | 1.5 g formula 21 | 0.12 g TDM | −274 | 5 | 44 | 3.4 | 8 |
| 13 | 1.5 g formula 23 | — | −279 | 2 | 68 | 2.7 | 11 |
| 14 | 1.5 g formula 23 | 0.02 g TDM | −283 | 3 | 33 | 3.1 | 9 |
| 15 | 1.5 g formula 23 | 0.12 g TDM | −273 | 6 | 36 | 3.3 | 11 |

ASV: Apparent surface voltage in volts after charging.
DD-1: Dark decay in the first second as a percentage of the ASV.
L-25: Quantity of light in mJ/m$^2$ in order to discharge the layer with a BRAUN flash type F900 to 25% of the ASV.
sigma: Surface discharge density in mC/m$^2$, measured after 1 second dark-decay.
Residual: Percentage of the ASV remaining after exposure with 100 mJ/m$^2$ (BRAUN flash type F900).

EXAMPLE 16

A charge generating layer was prepared which comprised as charge generating compound the bis-azo dye of formula 17 of the Formula sheet in the form of small pigment particles (approx. 0.2 μm) homogeneously distributed in a binder. For preparing that layer, 1 g of the said bis-azo dye was dispersed in 50 ml of 2% polymeric cellulose acetate butyrate in acetone by milling during 24 hours in a ball mill. The dispersion so obtained was applied by dip-coating to a conductive support (Melinex with a vapor-disposited aluminium layer).

The thickness of this charge generating layer after drying was 1.5 μm. To this charge generating layer a charge transporting layer was applied by dip-coating, employing the azine of formula 13 of the Formula sheet as the charge transporting agent. The application was effected by use of a solution of 25 ml of 10% "Lexan 141" in 1,2-dichloro-ethane, 1.5 g of said azine and 8 ml of tetrahydrofuran in which 0.03 g of the activator TDM (formula 14 of the Formula sheet) had been dissolved. After 15 minutes drying to the air the resulting double layer was dried in vacuo at 135° C. for 30 minutes.

By use of the resulting multi-layered electrophotographic element photocopies were made in an indirect electrophotographic photocopying machine, and the following points were checked: layer thickness, adhesion of the layers; charging; dark-decay; light-sensitivity; surface charge density; residual potential; memory effect; image quality of the copy obtained after transfer to plain paper, such transfer being of an image rendered visible on the charge transporting layer by application of a one-component developer, followed by fixation by heat and pressure; cleanability of the charge transporting layer; and permanence.

The results obtained with the electrophotographic element according to this example, as well as the results obtained with the elements according to the following Examples 17 to 21, are summarized after Example 21.

EXAMPLE 17

(Comparative Example)

Same as Example 16 except that instead of the azine of formula 13 of the Formula sheet, the tri-arylmethane of formula 23 of the Formula sheet was employed in the charge transporting layer.

EXAMPLE 18

A Charge generating layer was prepared comprising as charge generating compounds the bis-azo dye of formula 24 and the polymeric dye of formula 25 of the Formula sheet.

These dyes were dispered as small pigment particles (approx. 0.2 μm) in a binder which also comprised a charge transporting compound.

For preparing the charge generating layer, 2 g of "Lexan 141" and 1.2 g of the azine of formula 13 of the Formula sheet were successively dissolved in a mixture of 20 ml of tetrahydrofuran and 40 ml of 1,2-dichloroethane. Subsequently 1 g of the said bis-azo dye together with 1 g of the said polymeric dye were homogeneously distributed in the solution by milling in a ball mill during 24 hours.

The dispersion so obtained was applied by dip-coating to a conductive support (Melinex with a vapor-deposited aluminium layer). After drying the thickness of the charge generating layer was 1.3 μm. As in Example 16, a charge transporting layer was applied to the charge generating layer by dip-coating with use of the azine of formula 13 of the Formula sheet.

EXAMPLE 19

(Comparative Example)

Same as example 18, except that the tri-aryl methane of formula 23 of the Formula sheet instead of the said azine of formula 13 was used in both the charge generating layer and the charge transporting layer.

EXAMPLE 20

A charge generating layer was prepared comprising the metal-free phthalocyanine of formula 26 of the Formula sheet as the charge generating compound. For this purpose a thin layer of the metal-free phthalocyanine was deposited on a conductive support (Melinex with a vapor-deposited aluminium coating) by evaporation at a pressure of $10^{-5}$ to $10^{-6}$ torr. As in Example 16, a charge transporting layer was applied to the charge generating layer by dip-coating with use of the azine of formula 13.

EXAMPLE 21

(Comparative Example)

Same as example 20 except that the tri-arylmethane of formula 23 of the Formula sheet instead of the azine of formula 13 was used in the charge transporting layer.

the layers of Examples 16, 18 and 20 was excellent. For all layers the permanence upon partial charging was substantially higher than upon full charging.

The photo-electric results upon full charging are summarized in Table 3 below. The photo-electric results upon partial charging are summarized in Table 4 below.

TABLE 3

| Electrophotographic element | | | Maximum charging | | | | |
| --- | --- | --- | --- | --- | --- | --- | --- |
| Example | Charge-generating compound | Charge-transporting agent | ASV volts | DD-1 % | L-25 $mJ/m^2$ | sigma $mC/m^2$ | residual % |
| 16 | Pigment:formula 17 | formula 13 | −604 | 8 | 41 | 4.1 | 10 |
| 17 | Pigment:formula 17 | formula 23 | −542 | 8 | 79 | 4.6 | 16 |
| 18 | Pigment:formula 24 + formula 25 | formula 13 | −631 | 13 | 41 | 3.3 | 9 |
| 19 | Pigment:formula 24 + formula 25 | formula 23 | −711 | 12 | 49 | 3.4 | 11 |
| 20 | deposited by evaporation: formula 26 | formula 13 | −445 | 19 | 35 | 5.1 | 1 |
| 21 | deposited by evaporation: formula 26 | formula 23 | −550 | 11 | 38 | 5.3 | 3 |

TABLE 4

| Electrophotographic element | | | Partial charging (about 300 Volts) | | | | |
| --- | --- | --- | --- | --- | --- | --- | --- |
| Example | Charge-generating compound | Charge-transporting agent | ASV volts | DD-1 % | L-25 $mJ/m^2$ | sigma $mC/m^2$ | residual % |
| 16 | Pigment:formula 17 | formula 13 | −291 | 3 | 31 | 2.0 | 7 |
| 17 | Pigment:formula 17 | formula 23 | −288 | 2 | 80 | 2.1 | 18 |
| 18 | Pigment:formula 24 + formula 25 | formula 13 | −302 | 5 | 40 | 1.6 | 14 |
| 19 | Pigment:formula 24 + formula 25 | formula 23 | −313 | 4 | 48 | 1.5 | 18 |
| 20 | deposited by evaporation: formula 26 | formula 13 | −299 | 7 | 30 | 3.7 | 2 |
| 21 | deposited by evaporation: formula 26 | formula 23 | −295 | 2 | 44 | 3.1 | 8 |

ASV: Apparent surface voltage in volts after charging.
DD-1: Dark decay in the first second as a percentage of the ASV.
L-25: Quantity of light in $mJ/m^2$ in order to discharge the layer with a BRAUN flash type F900 to 25% of the ASV.
Sigma: Surface charge density in $mC/m^2$, measured after 1 second dark decay.
Residual: Percentage of the ASV remaining after exposure with 100 $mJ/m^2$ (BRAUN flash type F900).

RESULTS OF EXAMPLES 16 to 21

The charge transporting layers of Examples 16–21 all had a thickness of approximately 4 μm. The adhesion of the layers was excellent. The memory effect of the fully charged layers was extremely low for each example, and at partial charging memory effect was completely absent.

The layers of Examples 16, 18 and 20 could be cleaned easily after development with a one-component developer. The layers of the comparative Examples 17, 19 and 21 to the contrary could be cleaned only with great difficulties.

The copy quality for both full and partial charging of the layers of Examples 17, 19 and 21 was good, and of

EXAMPLE 22

The azines according to the structural formulas 2–11 of the Formula sheet have been tested in the way as described in example 2, however with the difference that instead of 1.5 g of the azine according to structural formula 13 2.1 g of each of the azines meant above was applied and that in the 8 ml tetrahydrofuran now 0.02 g of the activator TDM (formula 14 of the formula sheet) were dissolved.

All the 10 different electrophotographic elements prepared in that way appeared to yield good photocopies in an indirect electrophotographic photocopying machine.

Formula sheet

1. 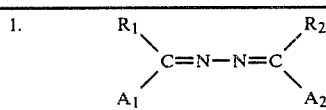

2. 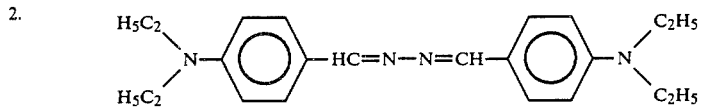

-continued
Formula sheet
3.
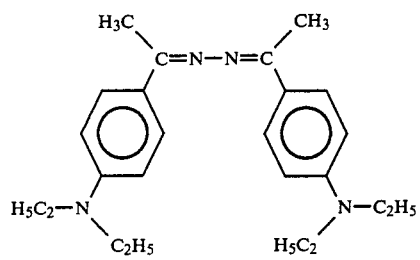
4.
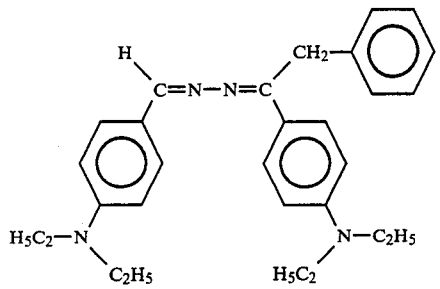
5.
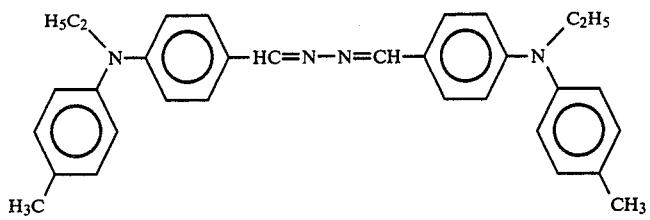
6.
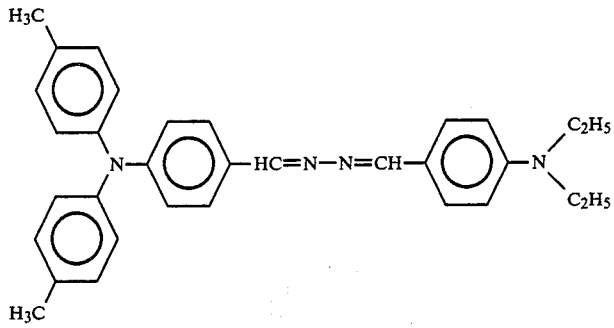
7.
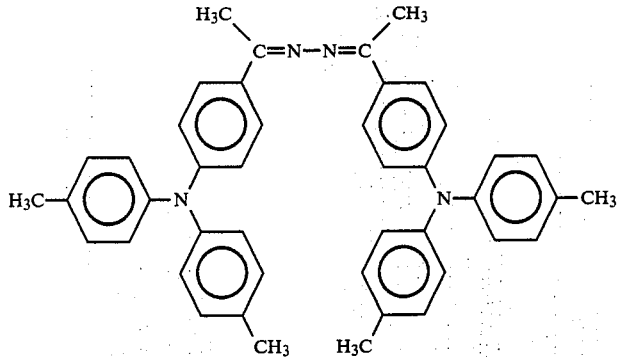

-continued
Formula sheet
8. 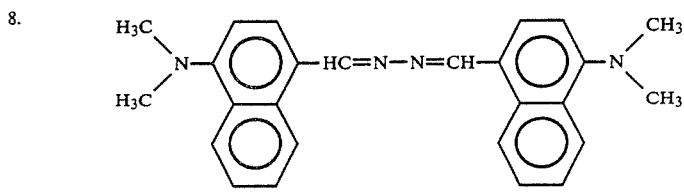
9. 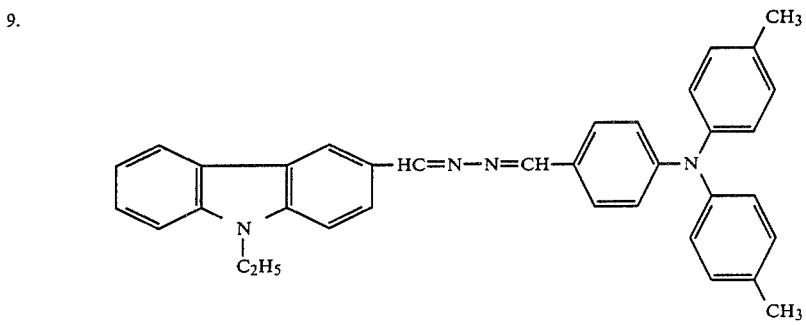
10. 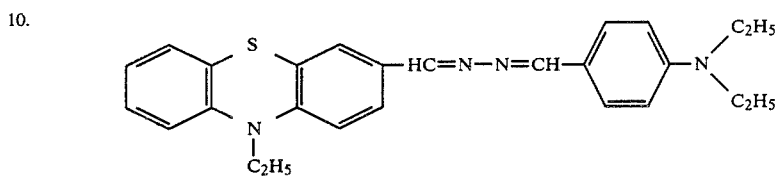
11. 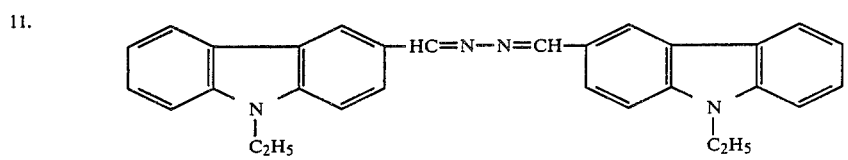
12. 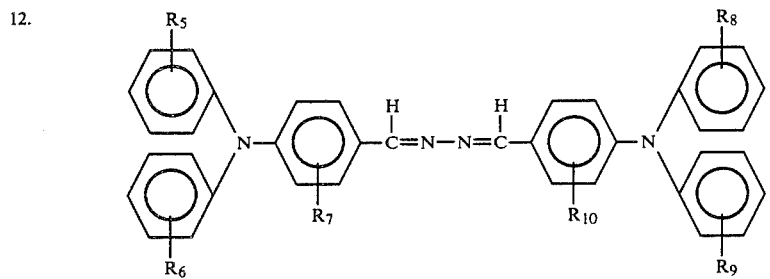
13. 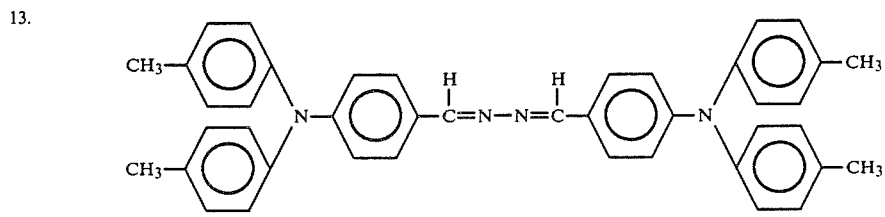
14. 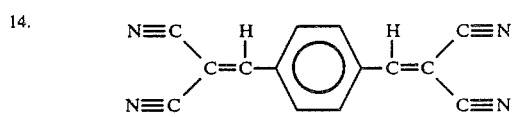

Formula sheet
15. 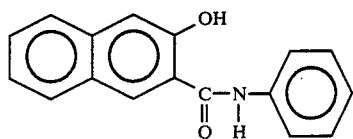
16. 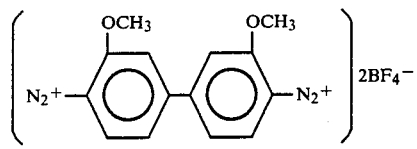
17. 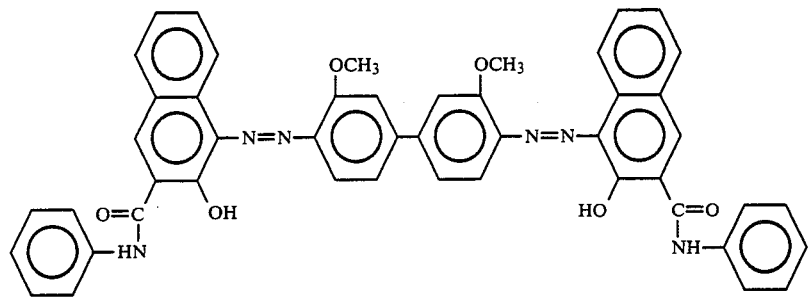
18. 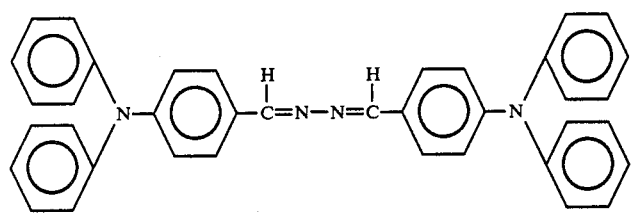
19. 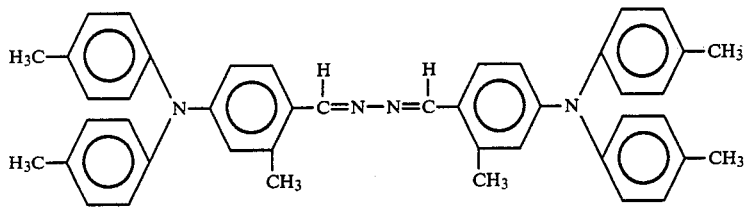
20. 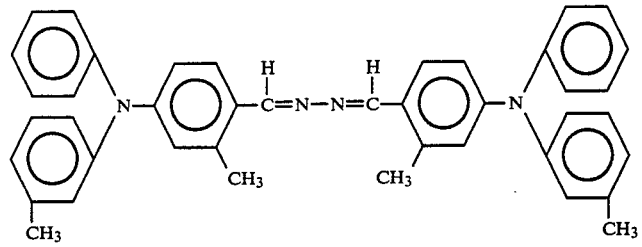
21. 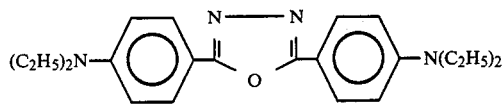
22. 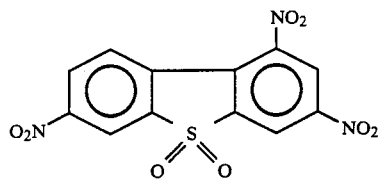

Formula sheet

23. 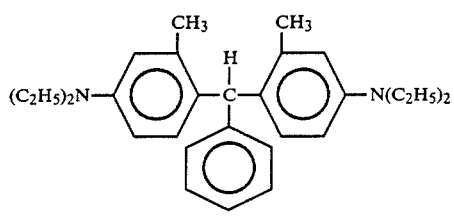

24. 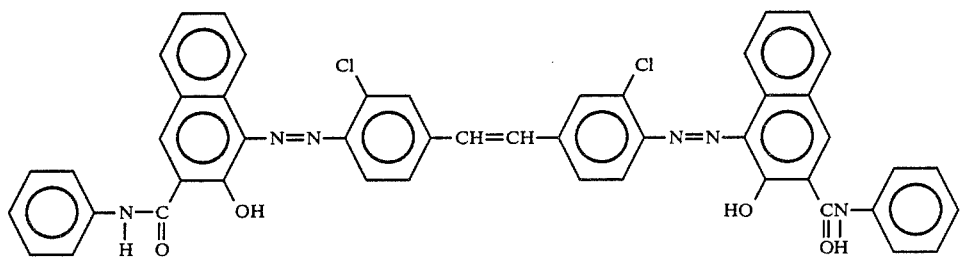

25. 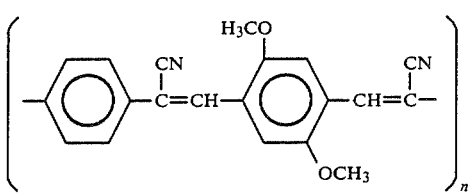

26. 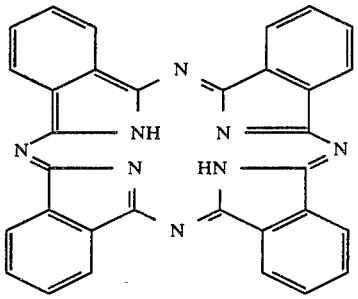

We claim:

1. A multi-layered electrophotographic element comprising an electrically conductive support carrying a photoconductive layer containing at least one radiation-sensitive charge generating compound, and applied to the photoconductive layer a charge transporting layer containing as a charge transporting agent homogeneously distributed in an insulating binder an azine which has the general structural formula

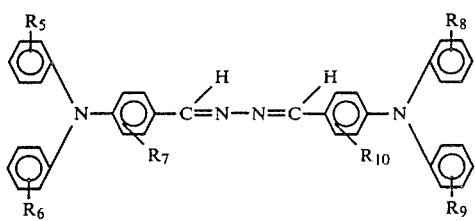

wherein $R_5$ to $R_{10}$ each represents a hydrogen atom or an alkyl group having 1 to 4 C atoms.

2. An element according to claim 1, said charge transporting agent being an azine of said formula 12 in which each of $R_5$, $R_6$, $R_8$ and $R_9$ is a methyl group.

3. An electrophotographic element according to claim 1, said azine being 4-[bis(4-methylphenyl)amino] benzaldehyde, azine.

4. An electrophotographic element according to claim 1, said charge transporting layer also containing an activator acting with said azine to enhance the discharge property of the element.

5. An electrophotographic element according to claim 4, said activator being the compound of formula 14 of the formula sheet.

6. An electrophotographic element according to claim 4, said activator being the compound of formula 22 of the formula sheet.

7. An electrophotographic element according to claim 2, said charge transporting layer also containing an activator acting with said azine to enhance the discharge property of the element.

8. An electrophotographic element according to claim 7, said activator being the compound of formula 14 of the formula sheet.

9. An electrophotographic element according to claim 3, said charge transporting layer also containing as an activator for said azine the compound of formula 14 of the formula sheet.

10. A multi-layered electrophotographic element comprising an electrically conductive support in the form of a drum or of a flexible web to be made endless for use, on said support a photo-conductive layer of 0.2 to 2 μm in thickness consisting essentially of at least one radiation-sensitive charge generating bis-azo compound homogeneously distributed in a polymeric binder, and on said photoconductive layer a charge transporting layer consisting essentially of an inert polymeric binder having homogeneously distributed therein about 20 to 40% by weight of 4-[bis(4-methylphenyl)amino] benzaldehyde azine and an activator for said azine.

11. A electrophotographic element according to claim 10, said activator being the compound of formula 14 of the formula sheet or the compound of formula 22 thereof, and the amount of activator being between 1 and 15% by weight based on the amount of said azine.

12. An electrophotographic element according to claim 10, said activator being the compound of formula 14 of the formula sheet and the amount of activator being between 0.5 and 3% by weight based on the amount of said azine.

13. An electrophotographic element according to claim 10, said photoconductive layer being a layer dip-coated on said support, said bis-azo compound being molecularly distributed in said photoconductive layer, and said charge transporting layer being a layer dip-coated on said photoconductive layer.

14. An electrophotographic element according to claim 12, said photoconductive layer being a layer dip-coated on said support, said bis-azo compound being molecularly distributed in said photoconductive layer, and said charge transporting layer being a layer dip-coated on said photoconductive layer.

15. A method of making photocopies which comprises substantially uniformly charging to not more than 70% of its maximum chargeable voltage a surface area of an electrophotographic element according to claim 4; then imagewise exposing said area and thereafter developing the resultant latent image with toner particles; then transferring the resultant powder image from said element for fixation to a receiving support; and then cleaning residual toner particles from said area before again charging it as aforesaid for making another copy.

16. A method of making photocopies which comprises substantially uniformly charging to not more than 70% of its maximum chargeable voltage a surface area of an electrophotographic element according to claim 9; then imagewise exposing said area and thereafter developing the resultant latent image with toner particles; then transferring the resultant powder image from said element for fixation to a receiving support; and then cleaning residual toner particles from said area before again charging it as aforesaid for making another copy.

17. A method of making photocopies which comprises substantially uniformly charging to not more than 70% of its maximum chargeable voltage a surface area of an electrophotographic element according to claim 10; then imagewise exposing said area and thereafter developing the resultant latent image with toner particles; then transferring the resultant powder image from said element for fixation of a receiving support; and then cleaning residual toner particles from said area before again charging it as aforesaid for making another copy.

18. A method of making photocopies which comprises substantially uniformly charging to not more than 70% of its maximum chargeable voltage a surface area of an electrophotographic element according to claim 12; then imagewise exposing said area and thereafter developing the resultant latent image with toner particles; then transferring the resultant powder image from said element for fixation to a receiving support; and then cleaning residual toner particles from said area before again charging it as aforesaid for making another copy.

19. A method according to claim 15, said toner particles being applied to said latent image from a one-component developer composed of finely divided, electrically conductive toner particles.

20. A method according to claim 18, said toner particles being applied to said latent image from a one-component developer composed of finely divided, electrically conductive toner particles.

* * * * *